United States Patent [19]

Grandics

[11] 4,423,208

[45] Dec. 27, 1983

[54] AFFINITY GEL-ADSORBENT

[76] Inventor: Peter Grandics, 260 S. 16th St., Philadelphia, Pa. 19102

[21] Appl. No.: 352,013

[22] Filed: Feb. 24, 1982

[51] Int. Cl.³ .............................................. C07J 17/00
[52] U.S. Cl. .................................. 536/5; 260/397.45; 536/6.1
[58] Field of Search ................. 536/5, 6.1; 260/397.45

[56] References Cited
FOREIGN PATENT DOCUMENTS
805830 12/1958 United Kingdom ........... 260/397.45

*Primary Examiner*—Elbert L. Roberts
*Attorney, Agent, or Firm*—Holland, Armstrong, Wilkie & Previto

[57] ABSTRACT

An improved affinity gel-adsorbent for use in an improved method of purifying glucocorticoid receptor by affinity chromatography and having the formula:

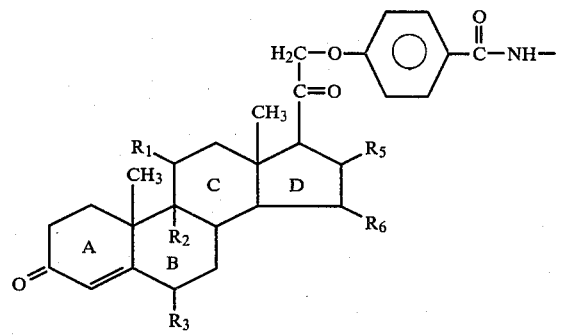

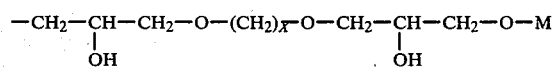

$R_1$: H or OH or =O
$R_2$: H or F
$R_3$: H or F
$R_4$: OH or H
$R_5$: OH or H

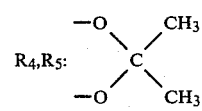

$R_6$: H or $CH_3$
X: 1 through 8
M: Matrix

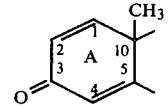

Alternative A ring with Δ1,2 double bond.

7 Claims, No Drawings

AFFINITY GEL-ADSORBENT

BACKGROUND OF THE INVENTION

This invention relates to an improved affinity gel-adsorbent for use in affinity chromatography. More particularly, this invention relates to an improved affinity gel-adsorbent for use in an improved method of purifying glucocorticoid receptor by affinity chromatography, said affinity gel-adsorbent having the above formula.

Cytosol is an extract of a cell. In the present case, it is a glucocorticoid receptor extract of a rat liver in the unactivated form or state which contains a plurality of proteins.

The involvement of proteins for glucocorticoids in intracellular action has been intensively studied during the past decade. However, basic to these studies is a knowledge of the molecular activities of these proteins, and their interrelationship with hormones, and the complexes they form in the cells under study. This involves the degree of concentration of the complexes formed, and the mechanism of the steroid hormone action with the receptor proteins. Much of the past work involved complexes of protein and steroid which were in the activated state. However, to obtain a true understanding of what is taking place in the cell itself requires a study of such complexes in the unactivated state as they appear in the natural cell itself, and from this, a better understanding of the biochemical mechanism of the process of forming the complex itself in its natural environment.

In the past, such complexes of hormones and receptor proteins were studies by affinity chromatography using an affinity gel-adsorbent prepared by cynogen bromide activation. However, the immobilized ligand leaks from their affinity matrix. This is a serious limitation for the use of affinity chromatography in the purification of hormone receptor proteins. An important improvement was achieved in the stability of the affinity adsorbent by attaching a substantially linear epoxy chain to the matrix, the former being terminated with an amino-functional group. Using such a technique, the possibility of leakage of the ligand was eliminated.

The steroid-receptor complex was obtained at an 46 percent overall yield, and the purification was about 1000-fold.

The following shows the synthesis route of the spacer arm, where M-(OH) is designated as the polymer matrix:

$$M-(OH) + \underset{O}{CH_2-CH-CH_2}-O-(CH_2)_4-O-CH_2-\underset{O}{CH-CH_2} \quad 1.$$

$$M-O-CH_2-\underset{OH}{CH}-CH_2-O-(CH_2)_4-O-CH_2-\underset{O}{CH-CH_2} + NH_3 \quad 2.$$

$$M-O-CH_2-\underset{OH}{CH}-CH_2-O-(CH_2)_4-O-CH_2-\underset{OH}{CH}-CH_2-NH_2 \quad 3.$$

The following is the formula of the affinity gel-matrix coupled to the preferred hormone.

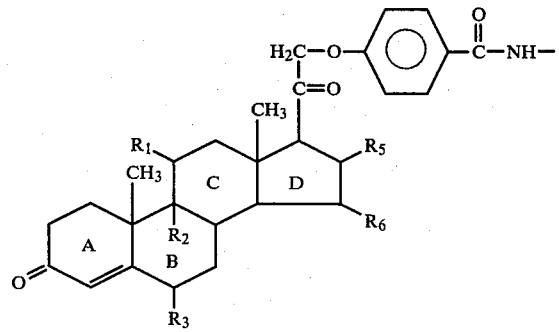

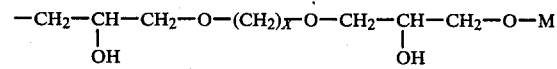

$R_1$: H or OH or =O
$R_2$: H or F
$R_3$: H or F
$R_4$: OH or H
$R_5$: OH or H

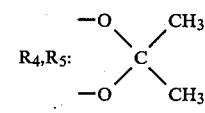

$R_6$: H or $CH_3$
X: 1 through 8
M: Matrix

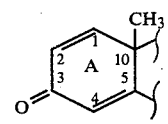

Alternative A ring with Δ1,2 double bond.

The process or procedure of this invention is based on the biospecific adsorption of proteins to a steroid ligand attached to a substantially linear epoxy chain anchored on polysaccharide matrix.

In the process of the present invention, the affinity gel-adsorbent is contacted with the cytosol containing the receptor proteins which are bound to the latter gel-adsorbent. The gel-bound receptor is eluted, after separation from the cytosol, with ($^3$H) triamcinolone acetonide, and further purified by agarose gel-filtration.

The protein yield obtained from the eluate was about 55 percent at 116-fold purification. However, when this was subjected to gel-filtration, the yield dropped to 46 percent but the purification of the proteins rose above 1000-fold.

DESCRIPTION OF A PREFERRED EMBODIMENT

The affinity gel-adsorbent of this invention, whose formula was heretofore illustrated, was prepared in the following manner, viz:

(A) COUPLING OF SPACER ARM TO MATRIX

In general, the agarose is reacted with 1,4-bis (2,3-epoxypropoxy) butane, and a primary amino-functional group is formed on the terminal end of the substantially linear epoxy chain with ammonia.

Specifically, 100 gms. of suction-dried Sepharose 2B was suspended in 130 ml of 0.5 M sodium hydroxide, and 20 ml of 1,4-bis (2,3-epoxypropoxy) butane was added to the latter solution. The resulting mixture was agitated for 2 hours at room temperature. The modified gel was washed with distilled water to neutrality, and traces of the epoxy compound were removed with 300 ml of acetone. The gel was allowed to stand in 150 ml of 12 M ammonia solution overnight, and washed with distilled water to a pH of 7. The amino content was found to be 2.9 μ mol per ml of packed gel using conventional procedures.

LIGAND PREPARATION

A. The steroid ligand was prepared as follows:

The C-21 corticosteroid chosen (0.01 mol) was dissolved in 50 ml dry pyridine and the solution was cooled to 0° C. Methanesulfonyl chloride (0.012 mol) was added and the solution was allowed to stand on ice for 2 hr in the dark. Subsequently, the mixture was poured onto 20-fold excess of ice cold water under continuous stirring. Precipitate was collected by filtration and was freed of pyridine by washing with 1 liter of ice cold water. Then, it was dried and weighed.

The product, was added with stirring in small portions to an equivalent amount of 0.03 M of the sodium salt of methyl-p-hydroxybenzoate dissolved in N,N'-dimethylformamide and reaction was completed at room temperature in 2 hrs. Further conventional procedures were followed as set forth in Proc. Nat'l Acad. Sci. USA, (1975) 72, 3845 to 3852. The end product possesses a carboxyl functional group attached to the steroid backbone through its 21-carbon atom.

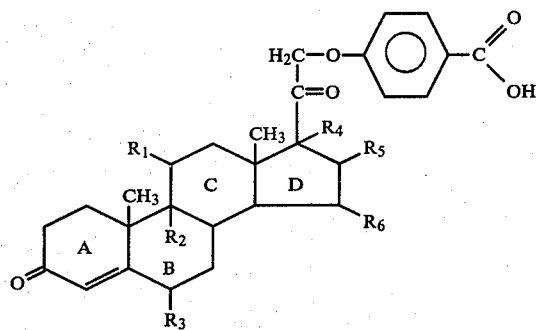

$R_1$: H or OH or=O
$R_2$: H or F
$R_3$: H or F
$R_4$: OH or H
$R_5$: OH or H

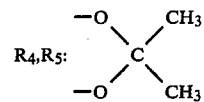

$R_6$: H or $CH_3$

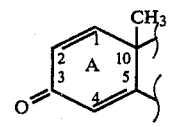

Alternative A ring with Δ1,2 double bond.

LIGAND COUPLED TO LINEAR EPOXY CHAIN ANCHORED ON THE AGAROSE MATRIX

Steroid ligand, 2.9 mmol, N-hydroxysuccimide, 3.2 mmol and N,N'-dicyclohexylcarbodiimide, 2.9 mmol were dissolved in 100 ml peroxide-free dioxane, and the resulting solution was allowed to stand overnight at 4° C. The precipitated N,N'-dicyclohexyl-urea was then filtered through type G-3 sintered glass, and washed with 5 ml of dioxane. The active ester was added with stirring to 100 gm of the amino-gel, produced above in the coupling stand of the linear chain to the matrix, contained in a mixture of dioxane and water; the latter in a ratio of 7:3, and a pH of 8 was maintained at all times with 1 M sodium bicarbonate. After 2 hours, the resulting mixture was poured into a Buchner filter, and washed successively with 3000 ml of 1:1 solution of dioxane and water. The coupled gel was allowed to stand over-night in 1500 ml of a 1 M sodium chloride solution, and then washed free of salt with distilled water. The steroid content of the gel was found to be 2.5 μmol per ml of packed gel by conventional procedures.

COMPLETION OF THE AFFINITY GEL-ADSORBENT

The ion-exchange properties of the residual amines was eliminated from the gel by suspending the same in a 0.1 M potassium phosphate buffer at a pH of 7.5, and acetylating with 250 μl of acetic anhydride. The end point of the reaction was detected by the 2,4,6-trinitrobenzene sulphonate test. The gel-adsorbent was then washed extensively with 3 liters of dioxane and 10 liters of 90 percent methanol in order to remove the steroid which was not covalently bound to the gel.

The resulting affinity gel-adsorbent, the formula as it heretofore apppears, can be stored for at least 1 year at 4° C. in a solution containing 10 mM 2-(N-morpholino) ethane sulphonic acid, 50 mM potassium fluoride, 0.5 mM ethylenediamine tetraacetic acid, and 0.5 mM dithiothreitol having a pH of 6.5.

As heretofore stated, in the purification process, the affinity gel-adsorbent of this invention is contacted with cytosol, the bound hormone receptor protein is eluted, and the latter further purified by gel-filtration.

CONTACTING

Note, all steps were carried out a 0° to 4° C.

2 ml. portions of the above affinity gel-adsorbent were mixed with 5 ml of cytosol with stirring for 2 hours.

ELUTING

The liquid is removed from the gel, and the latter is washed over a period of 30 minutes with 6 portions of 10 ml each of a buffer containing 10 mM 2(N-morpholino) ethanesulfonic acid, 50 mM potassium fluoride, 0.5 mM ethylenediamine tetraacetic acid, and 0.5 mM dithiothreitol having a pH of 6.5. After the washing, 2 ml of the latter buffer containing 2 $\mu$M (6,7-$^3$H) triamcinolone acetonide was added to the resulting mixture, and the latter allowed to stand for 16 hours at 0° C. The latter mixture is then filtered on a teflon filter, the gel washed with 1 ml of the above buffer, and the combined eluate was assayed for specific binding and protein content.

It was found that the yield was between 50 to 56 percent, and the unactivated receptor was purified 100 to 120-fold when compared to the crude cytosol.

GEL-FILTRATION

The eluate from the above affinity gel-adsorbent was further purified by filtration through an agarose Bio-Gel A-1.5 m column.

0.5 ml of the eluate was filtered through the column equilibrated with the above buffer. The column was 0.7 cm wide × 13 cm long with a 5 ml bed volume. The void volume was collected.

Aliquots of the latter were dissolved in the scintillation solution, and counted for radioactivity.

It was found that the proteins in the eluate was further purified by the latter step to a final purification of over 1000-fold when compared to the crude cytosol. The overall recovery of the present step was 80 to 85 percent of the eluate initially removed from the gel-adsorbent.

REGENERATION OF THE AFFINITY GEL-ADSORBENT

After separation of the eluate from the affinity gel-adsorbent, the latter was washed with 1 M sodium chloride to remove any protein therefrom. The collected adsorbents were stored in the same saline solution. After this, the adsorbents were transferred in a solvent mixture containing 30% trichloromethane, 45% methylalcohol, 10% Triton X-100, and 15% water. The gel was allowed to stand overnight at room temperature, and then washed with 30 ml of the latter solvent solution per 1 ml of packed adsorbent to remove (6,7-$^3$H) triamcinolone acetonide adsorbed during the purification process. Then, the affinity gel-adsorbent was successively washed with 90 percent methanol, distilled water, and a buffer containing 10 mM 2(N-morpholino) ethanesulfonic acid, 50 mM potassium fluoride, 0.5 mM ethylenediamine tetraacetic acid, and 0.5 mM dithiothreitol having a pH of 6.5. The regenerated adsorbent was then stored at 4° C. for reuse in the present process or procedure of this invention.

RESULTS AND OBSERVATIONS

TABLE 1

Fraction-volume-protein-receptor-specific activity-yield-purification

| | ml | mg/ml | dpm × 10$^{-4}$ bound | dpm × 10$^{-3}$ per mg-protein | % | fold |
|---|---|---|---|---|---|---|
| Cytosol | 5 | 21 | 267 | 25.43 | 100 | 1 |
| Cytosol treated with | 6.4 | 16 | 39.7 | 3.58 | | |

TABLE 1-continued

Fraction-volume-protein-receptor-specific activity-yield-purification

| | ml | mg/ml | dpm × 10$^{-4}$ bound | dpm × 10$^{-3}$ per mg-protein | % | fold |
|---|---|---|---|---|---|---|
| affinity gel | | | | | | |
| Affinity gel eluate | 4.2 | 0.119 | 147.7 | 2590 | 55 | 116 |
| Bio-Gel filtrate | 6.6 | 0.007 | 123.5 | 26548 | 46 | 1044 |

It has been found that the purified receptors exhibit properties similar to those in crude tissue extracts, that is, they retain their ability to undergo activation-dependent binding to isolated rat liver nuclei. Furthermore, purified complexes demonstrate the same sedimentation characteristics as cytosol receptor complexes.

BASIC PROCEDURES

Animals:

Male Wistar rats weighing between 150 to 200 gms were adrenalectomized. They were kept on normal rat chow, and water containing 0.9% sodium chloride. Within 5 to 10 days of adrenalectomy, they were sacrificed. Their livers were perfused in-situ via the portal vein with cold 0.9% sodium chloride, and then with the homogenization buffer containing 50 mM potassium fluoride, 50 mM 2(N-morpholino) ethanesulfonic acid, 1 mM ethylenediamine tetraacetic acid, and 5 mM dithiothreitol, pH 6.5.

Cytosol preparation:

The excised and minced livers from the above procedure were homogenized in 2 volumes of the buffer mentioned above. The homogenate was centrifuged for 10 minutes at 400 g, and the upper lipid layer was aspirated. The supernatant was centrifuged for 1 hour at 105,000 g to obtain the cytosol. All steps were performed between 0° to 4° C.

All glassware was siliconized twice by a 0.5% solution of dimethyl-dichlorsilane in absolute ether.

Having thus described my invention, I claim:

1. An improved affinity gel-adsorbent having the formula:

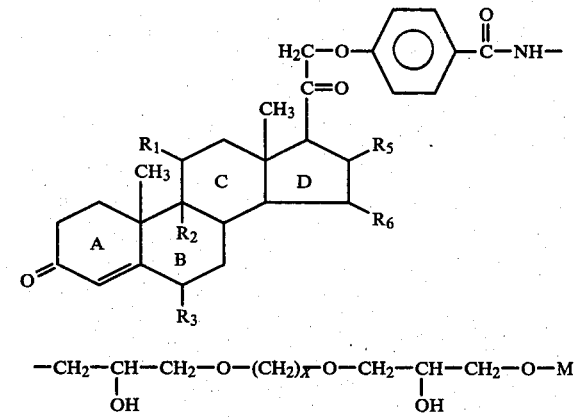

$R_1$: H or OH or=O
$R_2$: H or F
$R_3$: H or F

R4: OH or H
R5: OH or H

R4,R5: 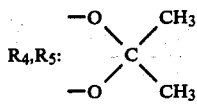

R6: H or CH3
X: 1 through 8
M: Matrix

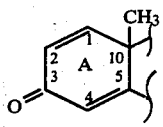

Alternative A ring with Δ1,2 double bond.
wherein M is a polysaccharide matrix including agarose, dextran, and cellulose.

2. An improved process of making an affinity gel-adsorbent comprising:
   A. coupling, in a pH range of 7 to 9, a steroid ligand having the following formula:

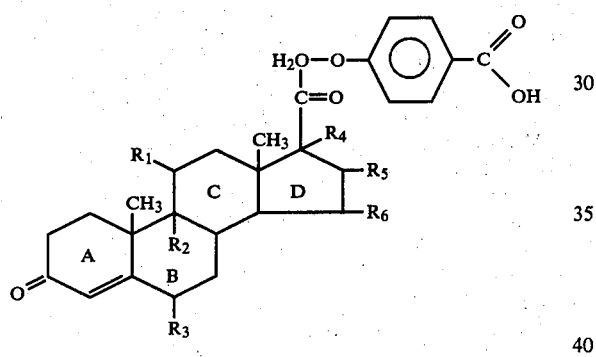

B. with an amino gel having the formula:

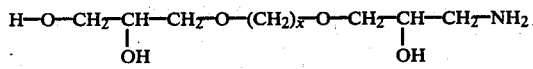

C. Wherein
     $R_1$: H or OH
     $R_2$: H or F
     $R_3$: H or F

R4: OH or H
R5: OH or H

R4,R5: 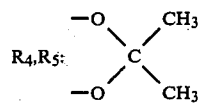

R6: H or CH3
M: agarose, dextran, or cellulose
X: 1 to 8

3. The process of claim 2 wherein A is

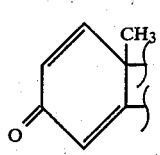

4. The process of claim 2 wherein said steroid ligand results when in first sequence C-21 corticosteroid is initially treated with methanesulfonyl in dry pyridine, and in second sequence with methyl-p-hydroxybenzoate sodium salt, and in third sequence with a molar excess of N-hydroxysuccinimide and an equimolar amount of $N,N^1$-dicyclohexylcarbodiimide in peroxide-free dioxane.

5. The process of claim 2 wherein in first sequence, said amino-gel results when said polysaccharide matrice are reacted with a di-epoxide having the formula

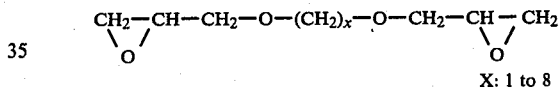

X: 1 to 8 in an alkaline medium, and in second sequence with ammonia, and in third sequence is suspended in a mixture of dioxane and water.

6. The process of claim 2 wherein said gel-adsorbent is successively washed in first sequence with dioxane and water and 1 M sodium chloride, and then acetylated with acetic anhydride, and finally washed with dioxane and methanol.

7. The process of claim 2 wherein said gel-adsorbent is regenerated after use with 1 M sodium chloride, distilled water and an organic mixture of chloroform, methanol, distilled water and treton X-100.

* * * * *